United States Patent [19]

Riitano et al.

[11] 3,962,790
[45] June 15, 1976

[54] ENDODONTIC INSTRUMENT

[75] Inventors: Francesco Riitano, Soverato; Nino Cassani, Bologna, both of Italy

[73] Assignees: s.r.l. C.I.R. (Cooperativa Industriale Romagnola), Italy, Italy; Dott. Francesco Riitano, both of Italy

[22] Filed: June 25, 1974

[21] Appl. No.: 483,035

[30] Foreign Application Priority Data
June 27, 1973    Italy.................................... 3440/73

[52] U.S. Cl............................................... 32/40 R
[51] Int. Cl.²......................................... N61C 17/00
[58] Field of Search........................ 32/40 R, 57, 58

[56] References Cited
UNITED STATES PATENTS

| | | | |
|---|---|---|---|
| 1,494,344 | 5/1924 | Deben............................... | 128/241 |
| 3,593,423 | 7/1971 | Jones................................... | 32/22 |
| 3,624,907 | 12/1971 | Brass et al............................ | 32/40 R |
| 3,745,655 | 7/1973 | Malmin................................. | 32/57 |

*Primary Examiner*—Robert Peshock
*Attorney, Agent, or Firm*—Robert E. Burns; Emmanuel J. Lobato; Bruce L. Adams

[57] ABSTRACT

An endodontic instrument for the irrigation of a dental radicular canal accompanied by aspiration of reflux liquid from said canals comprises at least two separate inlet ducts for irrigation liquid, and a third or outlet duct for aspiration of liquid reflowing from the irrigated radicular canals. It comprises further a needle holder head having two inner chambers, one communicating with the inlet ducts and the other one with the outlet duct. The head carries, firmly fixed thereto, a hollow needle for conveying the irrigation liquids to the radicular canal. The head has moveably fitted thereon an aspiration spout coaxial to the needle and movable in both directions with respect to the needle, as to make it possible to vary the depth of penetration of the needle into the radicular canal while the aspiration spout remains in a fixed position at the opening of the pulp cavity of the tooth.

5 Claims, 4 Drawing Figures

ENDODONTIC INSTRUMENT

BACKGROUND OF THE INVENTION

The present invention is of interest in endodontia, that is, that branch of dentistry which deals with endodonto-therapy, and relates in particular to an endodontic instrument for irrigation of a dental radicular canal with simultaneous aspiration of reflux liquid.

DESCRIPTION OF THE PRIOR ART

In endodontotherapy, irrigation offers the following positive aspects:

it ensures a first scouring out of the pulp chamber to better evidence the inlet of the radicular canal or canals to be drilled;

it facilitates the drilling process, lubricates the drilling tool, allows the milling of the endocanal matter, provides at the same time, during penetration and drilling, more or less consistent throwing out of material over the top of the opening, and removes and carries off to the outside organic residues and dental meal; and it makes it possible to realize even a chemical drilling (complementary to the mechanical one) using alternately a sodium hypochlorite solution and a hydrogen peroxide solution, the reaction between the two liquids forming nascent oxygen which, while frothing, cleans any angle not reached by mechanical drilling. The resulting effervescence obviously follows the line of least resistance, that is, the canal inlet, through which any residue present is washed away to the outside.

The irrigation needle does not obstruct this removal as long as it is freely seated in the canal and this is obtained by giving it an axial to-and-fro motion.

Combining the irrigation phase with simultaneous coaxial aspiration phase is useful for removing the reflux liquid, that is, to avoid any contact of the mucosa with medicinal substances of often an unpleasant taste and the possible swallowing of them together with the residues; at the same time this kind of aspiration eliminates the need for cotton wads and separate aspiration instruments, thereby easing the work of the operator and assistant.

Different instruments generally called "cannular syringes" have been designed for this purpose and have been studied to combine the two operations, that is, irrigation and aspiration.

The known instruments, however, do not satisfy the objects pursued herein, and in particular, the irrigation and aspiration ducts are statically kept at a reciprocally fixed and predetermined distance, thus limiting the penetration of the needle into the canal and the to-and-fro motion of the said needle, the only guarantee against the needle becoming blocked in the canal; further, the said known instruments do not make it possible to use two different irrigation liquids in rapid succession, that is, the above-quoted "chemical drilling".

Another drawback of the known instruments is that they are rather bulky, that the interchange and use of the points is difficult and that it is not very easy to take them apart for checking and cleaning the single parts.

SUMMARY OF THE INVENTION

The above outlined drawbacks and limits to the known instruments of this kind are now eliminated by the device of the present invention which, generally, comprises at least two ducts inside the body of the instrument for flow therethrough of at least two types of irrigation liquid without any possibility at all of the two liquids coming into contact at the inside of the said body; at least one third duct again inside the instrument body connected to an aspiration source for receiving the liquid reflowing from the previously irrigated dental radicular canals; and a needle holder head removably fixed to the body of the instrument and provided with at least two separate chambers, one communicating with the irrigation liquid ducts, the other one with the duct leading to the aspiration source. The head carries rigidly fixed thereto the needle for conveying the irrigation liquids into the dental radicular canals, and moveably fixed thereto an aspiration spout, which is coaxial to the needle and axially movable in both directions with respect to the needle: the relative, axial motion of the spout making it possible to continuously vary the depth of penetration of the needle into the dental radicular canals while the spout rests firmly seated on the inlet to the dental pulp cavity.

BRIEF DESCRIPTION OF THE DRAWINGS

The characteristics of the endodontic instrument of the present invention will be still better understood from the following description of a preferred embodiment thereof, without being limited thereto and on hand of the accompanying drawings in which.

DESCRIPTION OF THE PREFERRED EMBODIMENT

Figure 1:
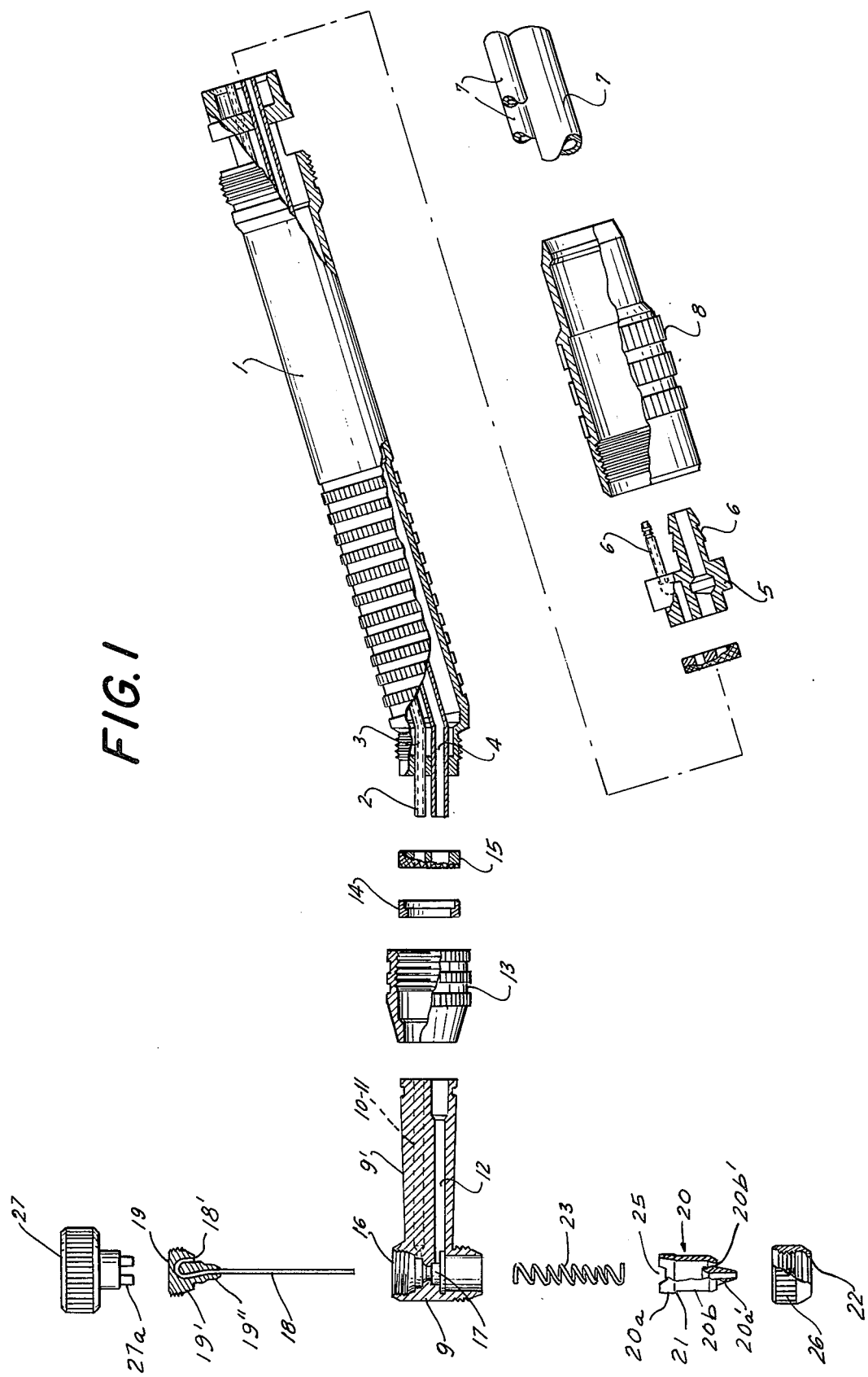
FIG. 1 is an exploded lateral view of the instrument of the present invention with some parts in section for better evidencing other ones.
Figure 2:
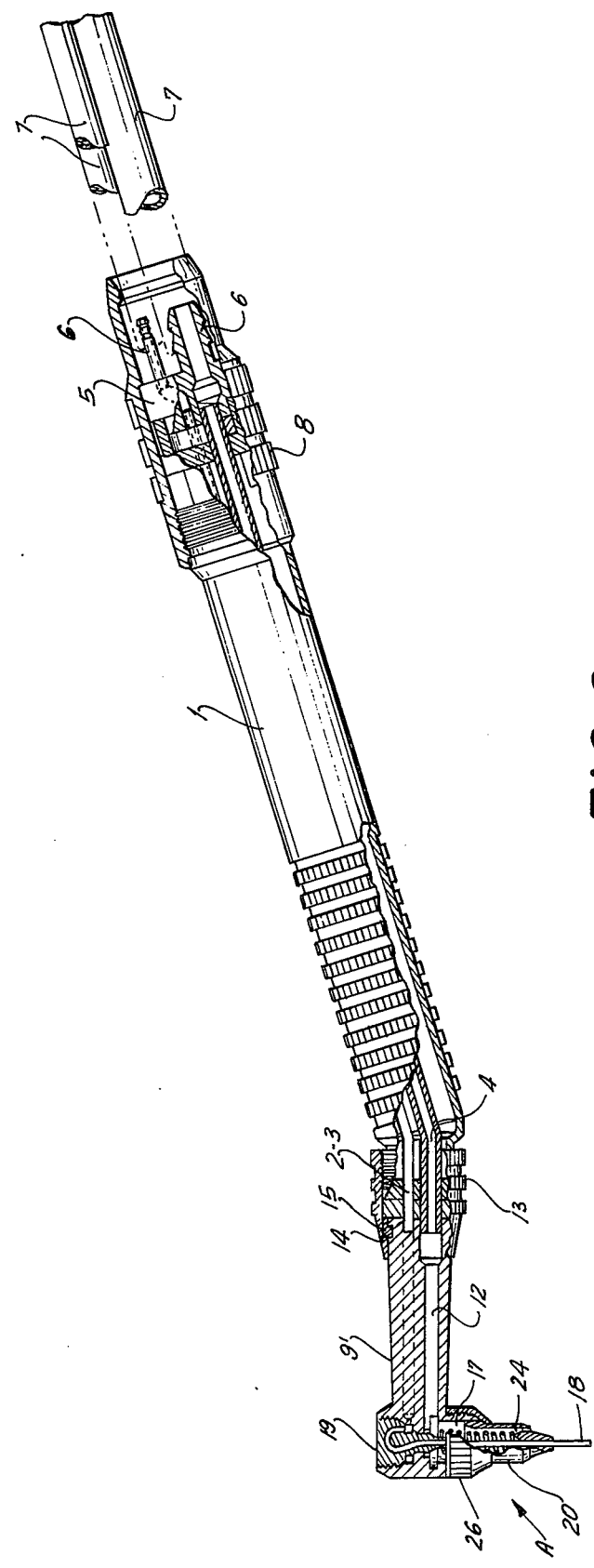
FIG. 2 is a lateral view of the instrument of FIG. 1 with some parts in section for better evidencing other ones.
Figure 3:
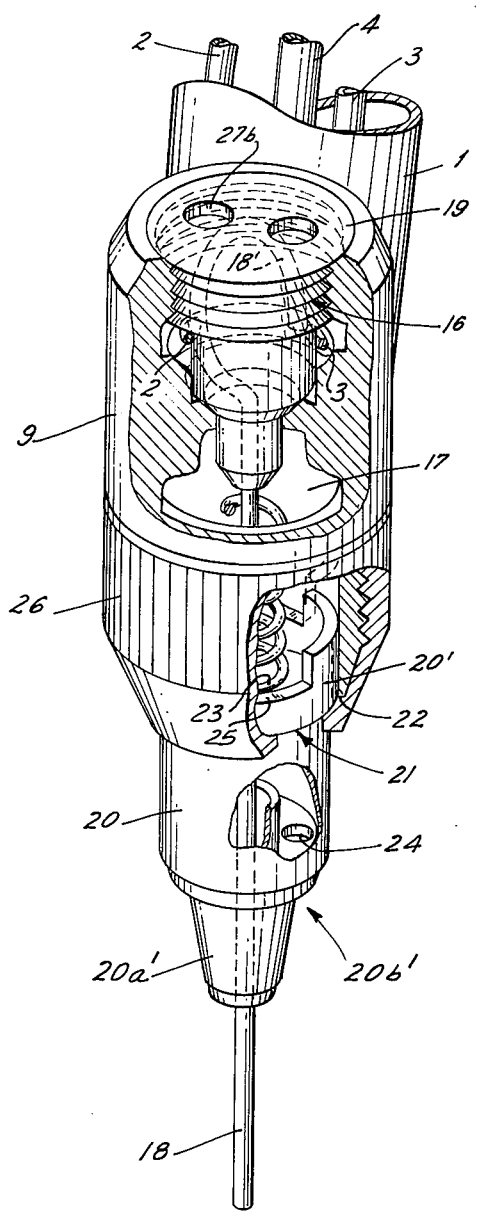
FIG. 3 is a perspective enlarged end view of a detail indicated with A in FIG. 2, with parts in section to better evidence other ones.
Figure 3A:
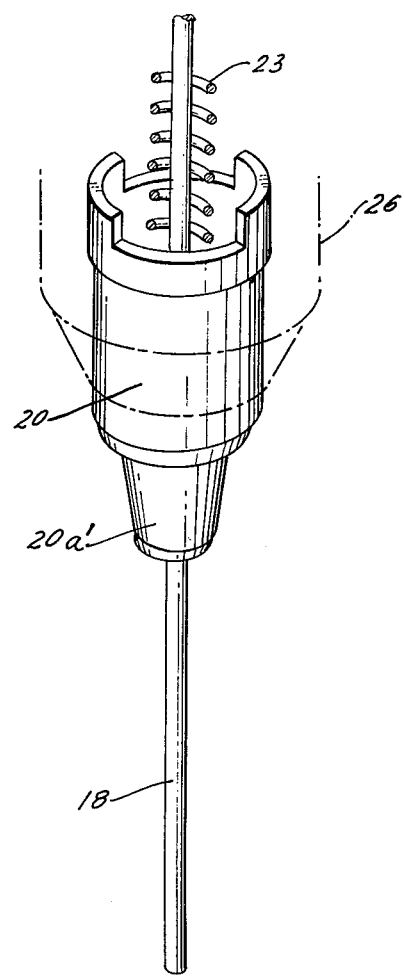
FIG. 3a is a view generally similar to that of FIG. 3, showing certain parts in a different relative position.

With reference to the said figures, 1 indicates the body of the instrument acting at the same time as handgrip thereof. At the inside, irrigator inlet ducts 2, 3 and aspiration duct 4 are suitably fixed to the front and rear ends of the body 1. To the rear end of the body 1 can be coupled a coupling 5 which receives the lower ends of the ducts 2, 3 and 4 and is at the same time fitted with nipples 6 to connect the said ducts to corresponding tubes 7 connected to a drive and control unit, not shown, which controls the irrigation and aspiration operations outlined hereinbelow.

A sleeve 8 which can be screwed on the body 1 covers the coupling 5 and rigidly fixes the said coupling 5 and the tubes 7 to the body 1 of the instrument.

The head of the instrument is shown at 9 and is fitted with a stem 9' containing three ducts or holes 10, 11 and 12, each of which can receive, coupled thereto, the front end of a duct 2, 3 and 4. The head 9 is fixed to the body 1 by means of a threaded locking ring 13 which can be screwed onto the body 1 and acts thereby on a ring 14 coupled to the stem 9' of the head 9; a washer 15 between the front end of the body 1 and the ring 14 ensures proper sealing of head 9 to body 1.

The head 9 has at the inside thereof: a first chamber 16 having an interiorly threaded end portion and laterally communicating with the ducts 10 and 11 and thereby with inlets 2, 3; and a second chamber 17 coaxial with chamber 16 and laterally communicating with the duct 12 and thereby with aspiration outlet 4.

The irrigator needle of the instrument as shown at 18. This needle which may have any suitable length, consists substantially of a tube, flexible as required and preferably of steel, seated at the upper end in a terminal or fitting 19 to be screwed into the chamber 16 of the head 9 and shaped so as to form a double seal 19', 19'' which prevents the irrigation liquids, from either (a) flowing out of the head along the screw threads of the terminal 19 or (b) passing into the chamber 17; the said liquids are thus forced to flow out through the tubular duct 18' of the needle 18. A moveable aspiration sleeve spout 20 can be inserted onto the needle 18, and moved axially to the latter. This spout is slidably secured to the head 9, and downward sliding out of the spout is prevented by means of a threaded locking ring 26 or stop ring 26 having an outer, knurled portion, the ring being screwed to the same head 9.

The body of the sleeve or spout 20 is substantially cylindrical and has sections of different external diameter, of which the upper one 20a corresponds to the section of the said second chamber 17 acting thus as a sliding guide for the said spout inside of the said chamber as explained hereinafter, a lower section 20b having smaller diameter.

The two sections 20a, 20b form a circular abutment 21 which together with a lower, inwardly projecting lip or ring 22 inside the threaded locking ring 26 prevents the spout 20 from becoming detached from the said locking ring 26 once the latter is fixed to the head 9.

A helical spring 23 presses the spout 20 resiliently, downwardly against the lip or ring 22.

At the lower end the spout 20 has a tapered section 20' surrounded by a peripheral annular crown 20b' which is provided with a number of holes 24 connecting the inner chamber of the spout 20 with the outside for aspiration of liquid reflowing from the dental radicular canal.

At the upper end the spout 20 has two slits 25 the purpose of which will explained hereinafter.

The operation of the instrument will now be described with reference to the objects it is intended to reach.

One of these objects is an instrument in which the irrigation duct 16, 18', 18 and the aspiration duct 24, 20, 17 are not rigidly fixed together; that is, an instrument permitting the free penetration of the needle 18 into the radicular canal to be treated, the to-and-fro motion in axial direction of the said needle in the canal with the possibility to control at any time its position and to avoid locking the needle in the canal, with the spout 20 of the aspiration duct 24, 17 firmly adhering to the opening of the pulp cavity of the tooth maintaining thus a constant aspiration and avoiding the possible contact of the mucosa with the employed medicinal substances which reflow to the surface.

It is a further object to supply an instrument with two irrigation ducts 2/3, 10/11 which allow in an easy and rapid way to convey at least two different types of irrigation liquid through a single needle 18 to the inside of the radicular canals to be treated with the possibility to ensure (using for example sodium hypochlorite and hydrogen peroxide) the reaction of the said liquids inside the said canals with the froth formed cleaning those recesses which are not reached by mechanical drilling alone.

It is a still further object hereof to supply an instrument which is easily taken apart for cleaning and checking of the individual component elements and in particular for exchanging the needles to be employed when hygienic and operational reasons require a single use of the needle.

The fact that the aspiration spout 20 is moveable with respect to the needle 18 makes it possible, while maintaining the said spout in a given position adhering to the opening of the pulp cavity of the tooth to be treated, to vary the depth of penetration of the needle in the cavity and to impress the needle with an alternate axial motion ensuring irrigation at different heights of the radicular canals.

Aspiration, even with the spout 20 fully retired within the head 9, that is, inside the chamber 17 of the head 9, is ensured by the slits 25 which in this case connect the spout 20 to the aspiration duct 12.

It is possible to convey two different types of the irrigation liquid to the inside of the cavity to be treated, through the two irrigation ducts 2 and 3 and then through the two irrigation channels 10 and 11 connected to the said two ducts and communicating with the chamber 16 of the head 9, hence with the needle 18. Thus we can have a first scouring with a medicament followed by a final washing out with a second liquid or else we can use the already mentioned chemical reaction cleaning on the basis of substances which react inside the cavity.

For this purpose the control station for the instrument object of the present invention is fitted with suitable control devices not shown, which make it possible to convey irrigation liquids in very short time intervals without omitting the continuous and simultaneous aspiration of the liquids reflowing to the surface, so that the said liquids will not mix inside the head 9.

The above description and the accompanying drawings clearly show the extreme ease with which the instrument can be taken apart for checking and cleaning.

By using an apposite key like 27 on the terminal 19, and thereby unscrewing the needle fitting 19 from the head 9, the latter is easily checked and the needle 18 replaced without having to act on the aspiration spout 20 or other parts of the instrument.

The above description clearly evidences that the instrument object of the present invention satisfies the intended objects giving at the same time the guarantee for optimal and safe use.

Obviously the present invention is not limited to the above-described preferred embodiment and variants of structural nature are foreseen without leaving the range of the present invention and claims.

What we claim and desire to secure by Letters Patent is:

1. An endodontic instrument, comprising;
   a head, defining an irrigation inlet chamber and, coaxially therewith, an aspiration outlet chamber, the head having a plurality of irrigation inlet ducts separate from one another, communicating with the inlet chamber, and aspiration outlet duct means communicating with the outlet chamber;
   a hollow irrigation needle coaxially secured to the head, having a needle inlet section communicating with the inlet chamber, the needle extending into, through and outwardly from the outlet chamber, said chamber being sealed from the inlet chamber and needle;

an aspiration sleeve coaxially surrounding the needle, surrounded by a part of the head which includes the outlet chamber, and extending outwardly from said part along a portion of the needle, said sleeve being coaxially slidable in the head, from a lowermost position of the sleeve to an uppermost position thereof relative to the head, the sleeve being apertured, on the outside of the head, for aspiration of fluid into the sleeve; and resilient means in the outlet chamber for urging the sleeve toward its lowermost position relative to the head to enable a point of the needle resiliently to penetrate variously from the sleeve into a radicular canal of a tooth to be treated while the sleeve remains in a fixed position at an opening of a pulp cavity of the tooth.

2. An instrument according to claim 1 including needle holder means threadedly secured to a portion of the inlet chamber, said holder means having the irrigation needle secured thereto and having the inlet section of the needle extending through the holder means.

3. An instrument according to claim 2 in which the needle holder means is disposed for sealing the inlet chamber from the outside of the head.

4. An instrument according to claim 2 in which the needle holder means is disposed for sealing the outlet chamber from the inlet chamber.

5. An endodontic instrument, comprising;

a head, defining an irrigation inlet chamber and, coaxially therewith, an aspiration outlet chamber, the head having irrigation inlet duct means communicating with the inlet chamber and aspiration outlet duct means communicating with the outlet chamber;

a hollow irrigation needle coaxially secured to the head, having a needle inlet section communicating with the inlet chamber, the needle extending into, through and outwardly from the outlet chamber, said chamber being sealed from the inlet chamber and needle;

an aspiration sleeve coaxially surrounding the needle, surrounded by a part of the head which includes the outlet chamber, and extending outwardly from said part along a portion of the needle, said sleeve being coaxially slidable in the head from a lowermost position of the sleeve to an uppermost position thereof relative to the head, the sleeve being apertured, on the outside of the head, for aspiration of fluid into the sleeve;

a locking ring threadedly secured to the head, around the outlet chamber;

a lip inwardly projecting from the locking ring to define the lowermost position of the aspiration sleeve relative to the head; and resilient means in the outlet chamber for urging the sleeve toward said lowermost position to enable a point of the needle resiliently to penetrate variously from the sleeve into a radicular canal of a tooth to be treated while the sleeve remains in a fixed position at an opening of a pulp cavity of the tooth.

* * * * *